United States Patent [19]
Aslam et al.

[11] Patent Number: 5,773,591
[45] Date of Patent: Jun. 30, 1998

[54] PROCESS FOR PREPARING COUMARIN SULFONATES

[75] Inventors: Mohammad Aslam; Michael T. Sheehan; George Kvakovszky, all of Corpus Christi, Tex.

[73] Assignee: Hoechst Celanese Corp., Somerville, N.J.

[21] Appl. No.: 813,106

[22] Filed: Mar. 7, 1997

[51] Int. Cl.$^6$ .................. C07D 311/20; C07D 335/06
[52] U.S. Cl. ................................................. 534/557
[58] Field of Search ................................ 534/557

[56] References Cited

U.S. PATENT DOCUMENTS

| | | | |
|---|---|---|---|
| 2,859,112 | 11/1958 | Sus et al. | 534/557 X |
| 4,211,791 | 7/1980 | Buckle et al. | 424/304 |
| 4,339,552 | 7/1982 | Balanson et al. | 430/192 |
| 4,588,670 | 5/1986 | Kelly et al. | 430/165 |
| 4,853,315 | 8/1989 | McKean et al. | 430/192 |
| 4,942,225 | 7/1990 | Lorenz | 534/560 |
| 5,501,936 | 3/1996 | Hosoda et al. | 430/191 |
| 5,532,107 | 7/1996 | Oie et al. | 430/192 |
| 5,541,033 | 7/1996 | Blakeney et al. | 430/192 |

FOREIGN PATENT DOCUMENTS

| | | |
|---|---|---|
| 2-61640 | 3/1990 | Japan. |
| 3-79670 | 4/1991 | Japan. |

OTHER PUBLICATIONS

A. Hermodson, W.M. Barker, K.P. Link/Studies of the 4–Hydroxycoumarins. Synthesis of the Metagolites and Some Other Derivatives of Warfarin—Journal of Medicinal Chemistry, 1971, vol. 14, No. 2, pp. 167–169.
Chemical Abstracts 113:68407 (1990).
Chemical Abstracts, 115:244059.

*Primary Examiner*—Fiona T. Powers

[57] ABSTRACT

A novel process for preparing sulfonic acid esters and amides of benzo-heterocyclic diazo diketo compounds, such as substituted diazo-4-oxo-3,4-dihydrocoumarins, which are useful synthetic intermediates in a wide variety of applications including photoresists, opto-electronics, agricultural, and pharmaceutical applications is disclosed and claimed. The process comprises the steps of (a) subjecting a substituted benzo-heterocyclic β-keto-enol compound to suitable diazo transfer conditions in the presence of a diazo transfer agent; (b) subjecting the so formed diazo diketo compound to suitable halosulfonation conditions in the presence of a halosulfonation agent; and (c) subjecting the so formed halosulfonyl aromatic compound to suitable substitution reaction in the presence of an alcohol or an amine to form the corresponding sulfonic acid ester or amide of benzo-heterocyclic diazo diketo compound. The compounds formed from the process of the present invention exhibit very high photosensitivity in the deep ultraviolet (DUV) region (ca. 250 nm), and therefore, are useful as photoactive compounds in DUV photoresist formulations.

19 Claims, No Drawings

PROCESS FOR PREPARING COUMARIN SULFONATES

BACKGROUND OF THE INVENTION

1. Field of the Invention

The present invention relates to a unique, novel, and cost effective process for preparing halosulfonyl and sulfonic acid esters or amides of 3-diazo-2,4-dioxo-benzo-heterocyclic compounds such as 3-diazo-4-oxo-3,4-dihydrocoumarins, which are useful synthetic intermediates in a wide variety of applications including photoresists, opto-electronics, agricultural, and pharmaceutical applications. More specifically, the present invention relates to a process for preparing sulfonic acid esters of 3-diazo-4-oxo-3,4-dihydrocoumarins which are useful as photoactive compounds in the photoresist formulations having applications in the deep ultraviolet region.

2. Description of the Prior Art

It is well known that diazo compounds are used as "photoactive-compounds" (PACs) in photoresist formulations. For example, diazonaphthoquinones (DNQs) are widely used as PACs in positive photoresist formulations. The DNQs, for example, contain a wide variety of ballast groups which can be tailored to adjust the solubility of DNQs before and after exposure to actinic radiation such as ultraviolet in the 360–450 nm region. The DNQs also undergo photochemical transformation when exposed to actinic radiation. Furthermore, when DNQs are blended with phenolic resins, they tend to promote the solubility of the phenolic resins after exposure to radiation. The unexposed DNQs having the ballast groups on the other hand inhibits dissolution of the phenolic resins. As a result, fine patterns (lines) can be formed using appropriate photomasks and actinic radiation sources, and such patterns are useful in semiconductor/microelectronics industry.

The commercially used photoresists containing the DNQs are frequently used in the 360–450 nm region of the electromagnetic spectrum. However, the current trend in the electronic industry is to develop semiconductor devices having extremely fine patterns. In order to obtain such fine patterns there is a need to develop photoresist formulation that can be developed in the 240–260 nm (i.e., the deep ultraviolet, DUV, region).

However, the currently commercially used DNQs, after exposure to light, absorb strongly between 240–260 nm region, and therefore, preclude their use as PACs in the DUV photoresist formulations. Therefore, it is an object of this invention to provide novel PACs which have no or minimal absorptions in the DUV region and thus are useful in DUV photoresist formulations. It is also an objective of this invention to provide a cost-effective, economic process for the preparation of the novel PACs of this invention.

PRIOR ART

The following references are disclosed as background prior art.

U.S. Pat. No. 4,211,791 discloses novel substituted coumarins and indanediones and a process for preparing them.

U.S. Pat. No. 4,339,522 discloses an ultraviolet lithographic resist composition and a process of making such composition which contains phenolic-aldehyde resins sensitized with Meldrum's diazo or a homologue thereof.

U.S. Pat. No. 4,588,670 discloses a light sensitive triester of o-quinone diazide containing positive photoresist compositions.

U.S. Pat. No. 4,853,315 describes o-quinone diazide sulfonic acid monoesters useful as sensitizers for positive resists. The esters of 1-oxo-2-diazo-naphthalene sulfonic acid in which the sulfonic acid group is either at 4- or the 5-position of a 3 (or 4)-hydroxymethyl-tricyclo[5.2.1.0.$^{26}$] decane are useful as sensitizers for positive resists, particularly at 365 nm.

U.S. Pat. No. 4,942,225 describes preparation of diazo and azo compounds using azidoformamidium salts.

U.S. Pat. No. 5,501,936 discloses positive-working quinonediazide photoresist composition containing a cyclohexyl-substituted triphenylmethane compound which is capable of giving an extremely fine patterned resist layer.

U.S. Pat. No. 5,532,107 describes positive resist composition containing photosensitive agents, which are quinonediazide sulfonates of tris- or tetra-hydroxy derivatives of triphenyl alkanes.

U.S. Pat. No. 5,541,033 discloses o-quinonediazide sulfonic acid esters of phenolic compounds and their use in radiation-sensitive compositions.

Japanese Laid-open Pat. No. Heisei 2-61640 discloses photosensitive compositions comprising an alkali-soluble resin and a photosensitizer having a 2-diazo-1,3-diketo group. Specific photosensitizer compounds included monosubstituted 3-diazo-4-oxo-3,4-dihydrocoumarins (examples of substituents included 7-methyl, 7-propyl, 7-methoxy, and 6-chloro). However, only the unsubstituted 3-diazo-4-oxo-3,4-dihydrocoumarin was used in the photoresist formulation.

Japanese Laid-open Pat. No. Heisei 3-79670 discloses a negative-type radiation sensitive resin composition containing radiation sensitive materials having a diazo keto group. Specific examples of radiation sensitive materials included substituted indanones, tetralones, tetrahydronaphthadiones, tetrahydroquinolones, and chromanones. Unsubstituted 3-diazo-4-oxo-3,4-dihydrocoumarin was also used as radiation sensitive material in this disclosure.

J. Med. Chem. 1971, Vol. 14, (pp. 167–168) describe the synthesis of 4,5-, 4,6-, or 4,7-dihydroxy coumarins.

All of the references described herein are incorporated herein by reference in their entirety.

SUMMARY OF THE INVENTION

Advantageously, the present invention provides a novel class of compounds which can function effectively as PACs in the DUV region. The compounds of the present invention are halosulfonyl and sulfonic acid esters or amides of fused benzo-heterocyclic diazo diketo compounds of the Formula IV as shown below:

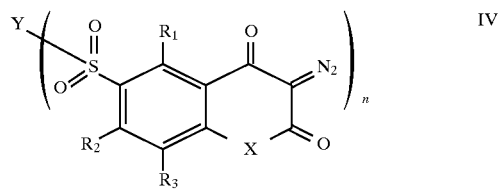

wherein:
(a) X is either oxygen or sulfur;
(b) Y is selected from the group consisting of a phenolic resin and a ballast group having the formula:
    $R_4$—(O)$_m$—, or $R_5$—($R_6$N)$_m$—, where
    (i) $R_4$ and $R_5$ are the same or different and are independently selected from the group consisting of:
    alkyl having 1 to 16 carbon atoms and valence of m, aryl having 6 to 24 carbon atoms and valence of m, and
aralkyl having 7 to 24 carbon atoms and valence of m;
(ii) $R_6$ is selected from the group consisting of:
hydrogen,
alkyl having 1 to 16 carbon atoms,
aryl having 6 to 24 carbon atoms, and
aralkyl having 7 to 24 carbon atoms; and
(iii) m is an integer having a value of 1 to 10; and
(c) $R_1$, $R_2$, and $R_3$ are the same or different and are independently selected from the group consisting of:
hydrogen,
fluorine, chlorine, bromine, or iodine,
linear or branched alkyl and fluoroalkyl groups having the formula $C_qH_xF_y$, where q is an integer from 1 to 8, x and y are integers from 0 to 2q+1, and the sum of x and y is 2q+1,
aryl having 6 to 10 carbon atoms,
aralkyl having 7 to 10 carbon atoms,
alkoxy having 1 to 8 carbon atoms,
aryloxy having 6 to 10 carbon atoms, and
aralkyloxy having 7 to 10 carbon atoms; and
(d) n is an integer having a value of 1 to 10.

In another aspect of this invention a process for the preparation of the novel sulfonic acid esters or amides of fused benzo-heterocyclic diazo diketo compounds of the present invention is also provided. Thus, the process for preparing the novel sulfonic acid esters or amides of fused benzo-heterocyclic diazo diketo compounds involves the steps of:

(a) subjecting a substituted benzo-heterocyclic β-keto-enol compound to suitable diazo transfer conditions in the presence of a diazo transfer agent for a sufficient period of time and under suitable conditions of temperature and pressure to form the corresponding diazo diketo compound;

(b) subjecting said diazo diketo compound to suitable halosulfonation conditions in the presence of a halosulfonation agent for a sufficient period of time and under suitable conditions of temperature and pressure to form the corresponding halosulfonyl diazo diketo compound; and (c) subjecting said halosulfonyl diazo diketo compound to suitable substitution reaction in the presence of an alcohol or an amine and a suitable base for a sufficient period of time and under suitable conditions of temperature and pressure to form the corresponding sulfonic acid ester or amide of fused benzo-heterocyclic diazo diketo compound.

DETAILED DESCRIPTION OF THE INVENTION

Unexpectedly, it has now been found that sulfonic acid esters or amides of fused benzo-heterocyclic diazo diketo compounds exhibit low or no absorptions in the deep ultraviolet region (DUV). In addition, a wide variety of mono- or polysulfonic acid esters or amides of these novel compounds can be readily made using a cost-effective, economic process. Thus, these compounds find utility as photoactive-compounds (PACs) in the DUV photoresist formulations.

The compounds of the present invention have the Formula IV as shown below:

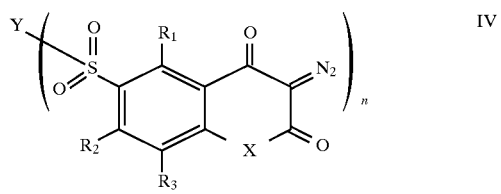

wherein:
(a) X is either oxygen or sulfur;
(b) Y is selected from the group consisting of a phenolic resin and a ballast group having the formula:
$R_4$—(O)$_m$—, or $R_5$—($R_6$N)$_m$—, where (i) $R_4$ and $R_5$ are the same or different and are independently selected from the group consisting of:
alkyl having 1 to 16 carbon atoms and valence of m,
aryl having 6 to 24 carbon atoms and valence of m, and
aralkyl having 7 to 24 carbon atoms and valence of m;
(ii) $R_6$ is selected from the group consisting of:
hydrogen,
alkyl having 1 to 16 carbon atoms,
aryl having 6 to 24 carbon atoms, and
aralkyl having 7 to 24 carbon atoms; and
(iii) m is an integer having a value of 1 to 10; and
(c) $R_1$, $R_2$, and $R_3$ are the same or different and are independently selected from the group consisting of:
hydrogen,
fluorine, chlorine, bromine, or iodine,
linear or branched alkyl and fluoroalkyl groups having the formula $C_qH_xF_y$, where q is an integer from 1 to 8, x and y are integers from 0 to 2q+1, and the sum of x and y is 2q+1,
aryl having 6 to 10 carbon atoms,
aralkyl having 7 to 10 carbon atoms,
alkoxy having 1 to 8 carbon atoms,
aryloxy having 6 to 10 carbon atoms, and
aralkyloxy having 7 to 10 carbon atoms; and
(d) n is an integer having a value of 1 to 10.

In the above definitions and throughout the present specification, alkyl means linear or branched alkyl having desirable number of carbon atoms and valence. Thus, a suitable $R_4$ or $R_5$ as specified herein may be an alkyl group having 1 to 16 carbon atoms of valence m, where m is an integer having a value of 1 to 10. The alkyl group is also often called as aliphatic group and may be acyclic (i.e., non-cyclic) or cyclic. Thus, suitable acyclic alkyl groups of valence I include methyl, ethyl, n- or iso-propyl, n-, iso-, or tert-butyl, linear or branched pentyl, hexyl, octyl, decyl, dodecyl, tetradecyl, and hexadecyl. The cyclic alkyl groups may be monocyclic or polycyclic. Suitable example of mono-cyclic alkyl groups include substituted cyclopentyl, cyclohexyl, and cycloheptyl groups. The substituents may be any of the acyclic alkyl groups described herein.

Suitable bicyclic alkyl groups include, without limitation, substituted bicyclo[2.2.1]heptane, bicyclo[2.2.2]octane, bicyclo[3.2.1]octane, bicyclo[3.2.2]nonane, and bicyclo [3.3.2]decane, and the like. Examples of tricyclic alkyl groups include, but not limited to, tricyclo[5.4.0.0.$^{2,9}$] undecane, tricyclo[4.2.1.2.$^{7,9}$]undecane, tricyclo[5.3.2.0.$^{4,9}$] dodecane, and tricyclo[5.2.1.0.$^{2,6}$]decane. As mentioned herein, the cyclic alkyl groups may additionally contain any of the acyclic alkyl groups as substituents.

The multivalent alkyl groups are derived from any of the alkyl groups mentioned hereinabove. Accordingly, a divalent acyclic group may be methylene, 1,1- or 1,2-ethylene, 1,1-, 1,2-, or 1,3 propylene, and so on. Similarly, a divalent cyclic alkyl group may be 1,2- or 1,3-cyclopentylene, 1,2-, 1,3-, or 1,4-cyclohexylene, and the like. A divalent tricyclo alkyl group may be any of the tricyclic alkyl group mentioned hereinabove. A particularly useful tricyclic alkyl group in this invention is 4,8-bis(methylene)-tricyclo[5.2.1.0.$^{2,6}$]decane.

Suitable examples of monovalent aryl group having 6 to 24 carbon atoms include phenyl, tolyl, xylyl, naphthyl, biphenyls, bis-phenyls, tris-phenyls and the like. These aryl groups may further be substituted with any of the appropriate alkyl or aryl groups mentioned hereinabove. Similarly, appropriate polyvalent aryl groups as desired may be used in this invention. Representative examples of divalent aryl groups include phenylenes, xylylenes, naphthylenes, biphenylenes, and the like.

Representative examples of monovalent aralkyl having 7 to 24 carbon atoms include phenylmethyl, phenylethyl, diphenylmethyl, 1,1- or 1,2-diphenylethyl, 1,1-, 1,2-, 2,2-, or 1,3-diphenylpropyl, and the like. Appropriate combinations of substituted aralkyl groups as described herein having desirable valence may be used as a polyvalent aralkyl group.

Suitable alkyl, aryl or aralkyl substituents as $R_1$, $R_2$, and $R_3$ may be the same as described herein. Representative examples of linear or branched fluoroalkyl groups having 1 to 8 carbon atoms include, for example, trifluoromethyl, 1,1,2-trifluoroethyl, pentafluoroethyl, perfluoropropyl, perfluorobutyl, and 1,1,2,3,3-pentafluorobutyl.

As used herein, alkoxy means straight or branched chain alkoxy having 1 to 10 carbon atoms, and includes, for example, methoxy, ethoxy, n-propoxy, isopropoxy, n-butoxy, isobutoxy, tert-butoxy, pentyloxy, hexyloxy, heptyloxy, octyloxy, nonyloxy, decanyloxy, 4-methylhexyloxy, 2-propylheptyloxy, and 2-ethyloctyloxy.

Examples of aryloxy having 6 to 10 carbon atoms may include phenoxy, tolyloxy, xylyloxy, and the like. Examples of aralkyloxy having 7 to 10 carbon atoms include phenylmethoxy, α- or β-phenethyloxy, 2-phenylpropyloxy, and the like.

Furthermore, and as used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Particularly preferred compounds of this invention are those in which $R_1$ to $R_3$ are unsubstituted, i.e., in these compounds $R_1$ to $R_3$ are hydrogen. Also, the preferred compounds of this invention are 3,4-dihydrocoumarin derivatives, i.e., X is oxygen in Formula IV. In one of the preferred embodiments a particularly useful compound is 6-chlorosulfonyl-3-diazo-4-oxo-3,4-dihydrocoumarin having the formula:

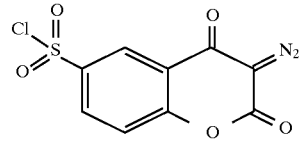

In another embodiment of this invention Y is a ballast group. As described herein, a ballast group is intended to mean a wide variety of alkyl, aryl, or aralkyl groups of desirable valence as described hereinabove. Any of the ballast groups well known in the art may be used. A number of different ballast groups are described in U.S. Pat. No. 4,588,670; U.S. Pat. No. 4,853,315; U.S. Pat. No. 5,501,936; and U.S. Pat. No. 5,532,107; all of which are incorporated herein by reference in their entirety.

It is believed that judicious selection of the ballast group is extremely critical to obtain desired intended benefit from the 3,4-dihydrocoumarin compound. The ballast group plays several roles particularly if it is used in the photoresist formulation. It is believed that the appropriate selection of ballast group can affect the solubility of the photoresist formulation formed therefrom. The ballast group further affects the shelf/formulation stability as well as the thermal stability of the photoresist formulation.

Suitable ballast groups that may be used in this invention, for example, may be selected from the group consisting of aromatic or aliphatic monohydroxy compounds, dihydroxy compounds, trihydroxy compounds, tetrahydroxy compounds, pentahydroxy compounds, hexahydroxy compounds, heptahydroxy compounds, octahydroxy compounds, nonahydroxy compounds, decahydroxy compounds, monoamines, diamines, triamines, tetraamine, pentaamines, hexaamines, octamines, and decaamines. Preferably, the ballast groups are aromatic or aliphatic polyhydroxy compounds as described herein, i.e., either polyalcohols or polyphenols. Most preferably, the ballast groups are polyhydroxy aliphatic compounds having at least two hydroxy groups.

In yet another preferred embodiment, the preferred compounds of this invention are sulfonic acid esters of substituted 3-diazo-4-oxo-3,4-dihydrocoumarin of the formula:

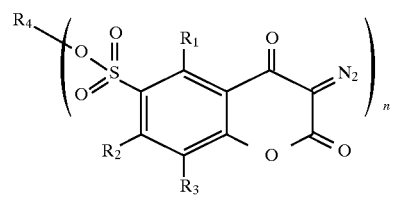

wherein $R_1$, $R_2$, $R_3$, $R_4$, and "n" are as defined hereinabove. Preferably, the value of "n" in this embodiment is 1 to 8. In this embodiment, the ballast group, $R_4$, is selected from the group consisting of phenols; cresols; catechols; resorcinols; hydroquinones; pyrogallols; phloroglucinols; mono-, di-, trihydroxynaphthalenes; mono-, di-, tri- and tetrahydroxy biphenylenes, tris(hydroxyphenyl)alkanes; polyhydroxy bisphenyls of the formula:

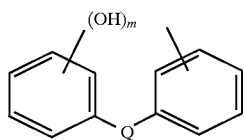

where:

(a) Q is selected from the group consisting of —O—, —S—, —SO$_2$—, —SO—, —CO—, an alkylene group containing 1 to 6 carbon atoms, an alkylidene group containing 1 to 6 carbon atoms, and an aralkylidene group containing 7 to 20 carbon atoms; and (b) m is an integer having a value of 1 to 8; and substituted tricyclo[5.2.1.0$^{2,6}$]decane of the formula:

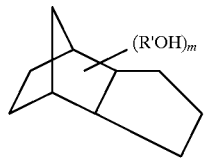

where:

(a) R' is a linear or branched alkyl or fluoroalkyl group having the formula $C_qH_xF_y$, where q is an integer from 1 to 4, x and y are integers from 0 to 2q+1, and the sum of x and y is 2q+1; and (b) m is an integer having a value of 1 to 8.

In this preferred embodiment, specific examples of $R_4$ group may be selected from the group of polyhydroxy aromatic or aliphatic compounds listed below:

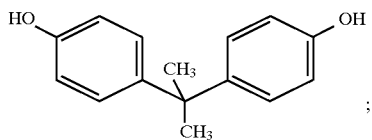

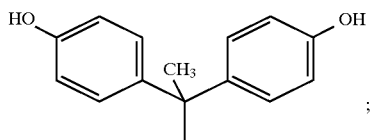

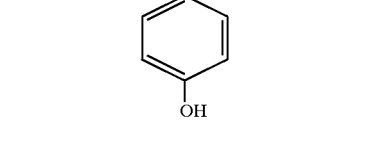

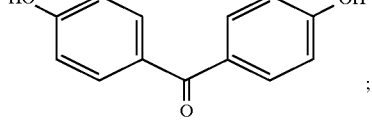

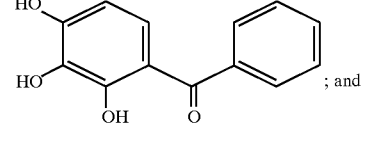

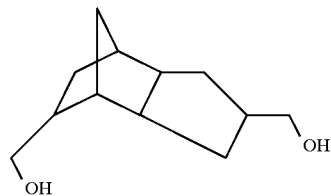

In one of the most preferred embodiments the 3-diazo-4-oxo-3,4-dihydrocoumarinsulfonic acid esters of the present invention are unsubstituted and have the following formula:

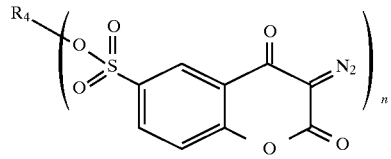

wherein $R_4$ and n are as defined above. Unexpectedly and surprisingly it has now been found that proper selection of $R_4$ can have a great effect on the solubility of the PAC formed therefrom before and after exposure to DUV light. Accordingly, particularly, preferred $R_4$ in this embodiment is at least a divalent alkyl, aryl or aralkyl group, i.e., n=2. Most preferably, n has a value of 2 to 6 in this embodiment. Also, preferred alkyl groups in this preferred embodiment are those which have at least 6 carbon atoms.

As specific examples of sulfonic acid esters of 3,4-dihydrocoumarins in this preferred embodiment, following compounds may be mentioned:

bis(6-sulfonyl-3-azo-4-oxo-3,4-dihydrocoumarin) bisphenol-A having the formula:

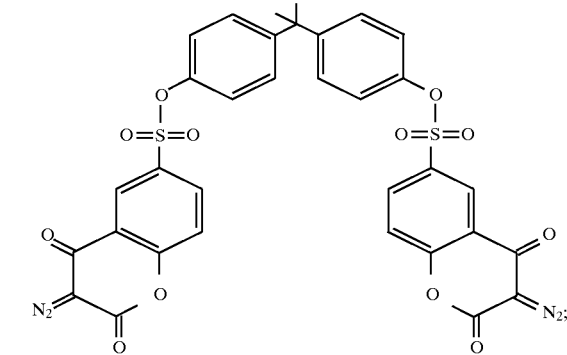

1',1',1'-tris-4-(3-diazo-4-oxo-3,4-dihydrocoumarin-6-sulfonyloxyphenyl)ethane having the formula:
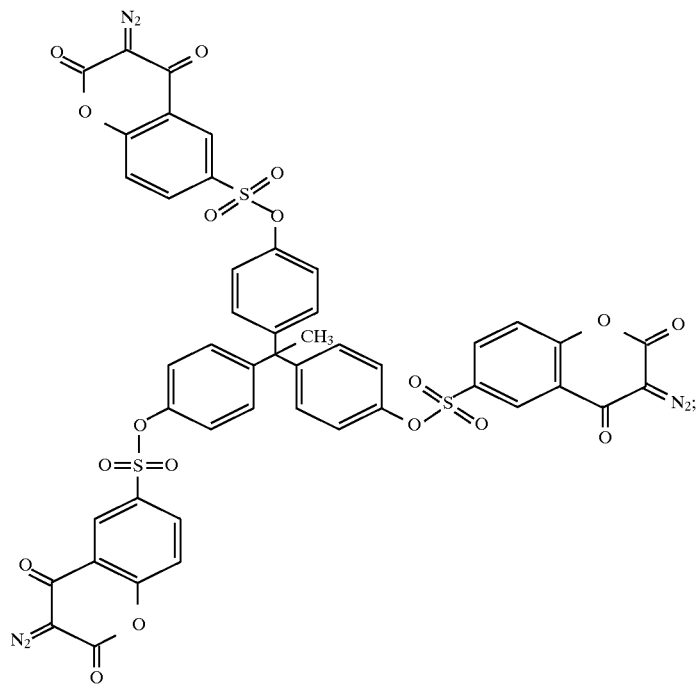
4,4'-bis(3-diazo-4-oxo-3,4-dihydrocoumarin-6-sulfonyloxy)benzophenone having the formula:
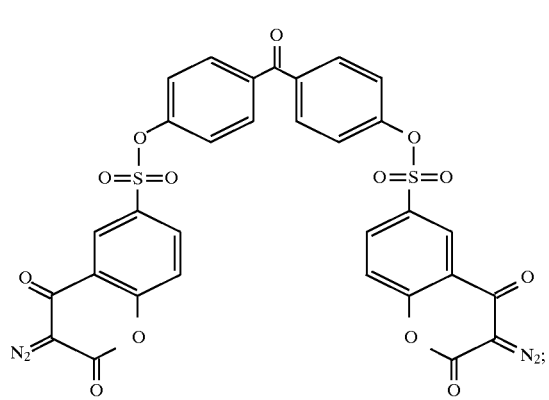
2,3,4-tris(3-diazo-4-oxo-3,4-dihydrocoumarin-6-sulfonyloxy)benzophenone having the formula:
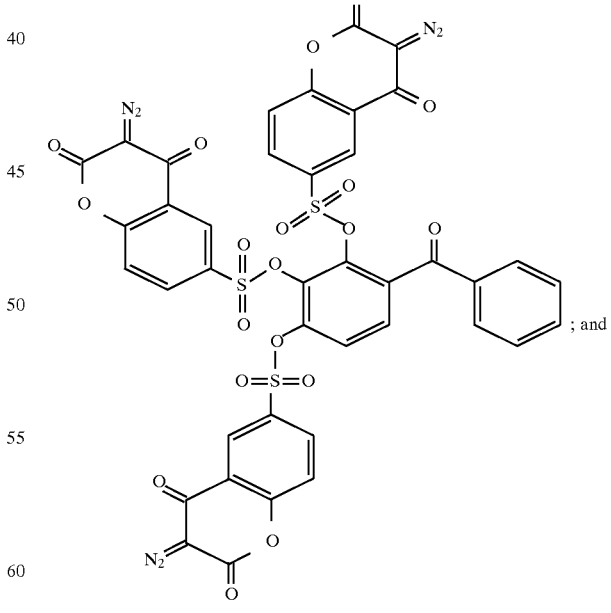
; and
4,8-bis(3-diazo-4-oxo-3,4-dihydrocoumarin-6-sulfonyloxymethyl)tricyclo[5.2.1.0.$^{2,6}$]decane having the formula:

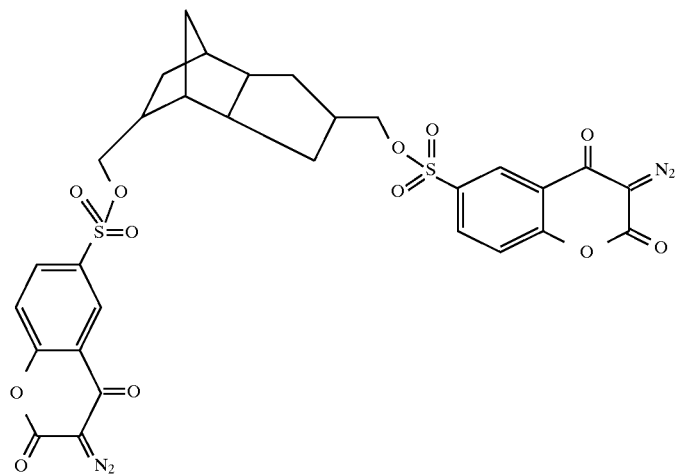

When polyhydroxy compounds are used as the ballast groups, sometimes it is advantageous that not all of the hydroxy groups are esterified with the 3,4-dihydrocoumarinsulfonyl chloride. Representative examples of partially esterified 3,4-dihydrocoumarinsulfonates include, but not limited to, 1'1'-bis-4-(3-diazo-4-oxo-3,4-dihydrocoumarin-6-sulfonyloxyphenyl)-1'-(4-hydroxyphenyl)ethane having the formula:

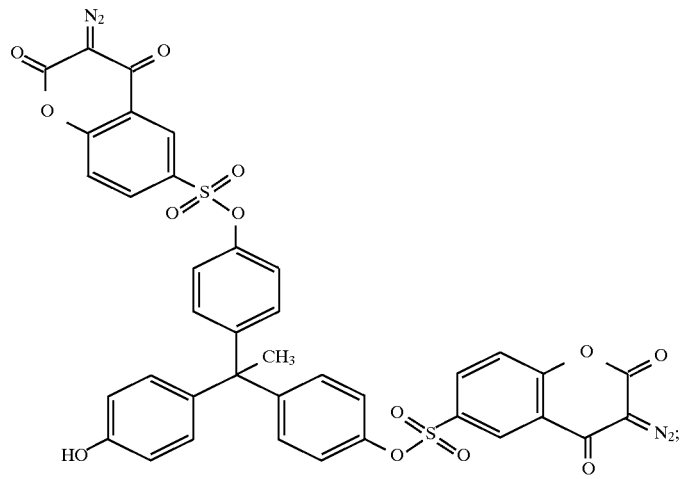

1'-4-(3-diazo-4-oxo-3,4-dihydrocoumarin-6-sulfonyloxyphenyl)-1',1'-bis(4-hydroxyphenyl)ethane having the formula:

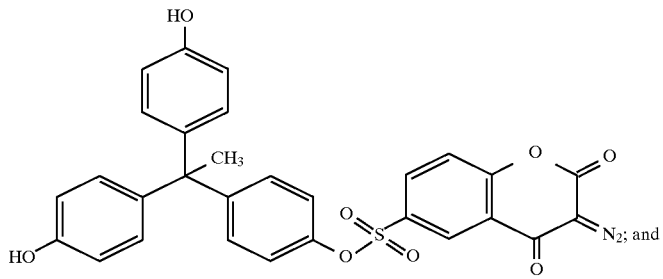

4-(3-diazo-4-oxo-3,4-dihydrocoumarin-6-sulfonyloxymethyl)-8-(hydroxymethyl)tricyclo[5.2.1.0.$^{2,6}$] decane having the formula:

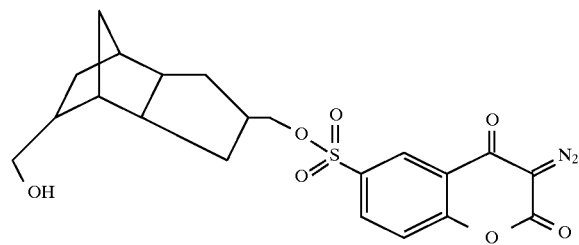

A wide variety of phenolic resins may also be used to form esters of 3,4-dihydrocoumarinsulfonates of the present invention. Any phenolic resin that is known in the art which will react with the halosulfonyl 3,4-dihydrocoumarin compound of this invention may be used. Phenolic resins that are suitable for this purpose may be selected from the group consisting of novolak resins; poly(4-hydroxystyrene); copolymers of hydroxystyrene and a member selected from the group consisting of acrylate, methacrylate and mixtures thereof; poly(hydroxystyrene-co-t-butyloxycarbonyloxystyrene); poly(hydroxystyrene-co-hydroxymethylstyrene); poly(hydroxystyrene-co-acetoxymethylstyrene); alkyl substituted polyvinyl phenols; and the like.

A particularly preferred phenolic resin is poly(4-hydroxystyrene) and the resulting sulfonate ester has the formula:

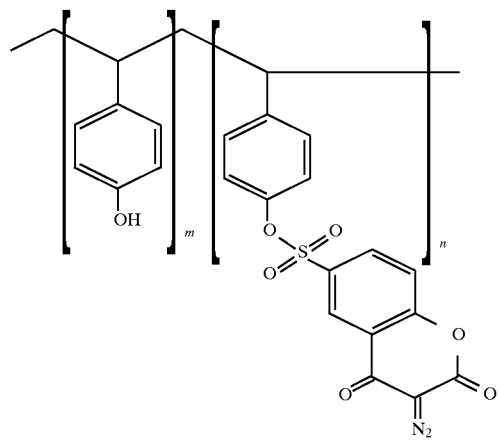

where m is an integer having a value of 25 to 200, and n is an integer having a value of 1 to 10.

In another facet of this invention there is also provided a novel, unique, and efficient process for preparing sulfonic acid ester or amide of fused benzo-heterocyclic diazo diketo compounds comprising the steps of:

(a) subjecting a substituted benzo-heterocyclic β-keto-enol compound to suitable diazo transfer conditions in the presence of a diazo transfer agent for a sufficient period of time and under suitable conditions of temperature and pressure to form the corresponding diazo diketo compound;

(b) subjecting said diazo diketo compound to suitable halosulfonation conditions in the presence of a halosulfonation agent for a sufficient period of time and under suitable conditions of temperature and pressure to form the corresponding halosulfonyl diazo diketo compound; and (c) subjecting said halosulfonyl diazo diketo compound to suitable substitution reaction in the presence of an alcohol or an amine and a suitable base for a sufficient period of time and under suitable conditions of temperature and pressure to form the corresponding sulfonic acid ester or amide of fused benzo-heterocyclic diazo diketo compound.

The starting material, i.e., the substituted benzo-heterocyclic β-keto-enol compound has the formula:

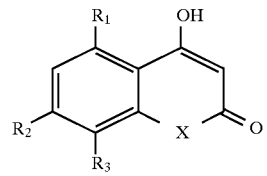

wherein X, $R_1$, $R_2$, and $R_3$ are as defined hereinabove.

Utilizing the substituted benzo-heterocyclic β-keto-enol compound (Formula I) it is believed that the process of the present invention proceeds as shown in Scheme I below:

Scheme I

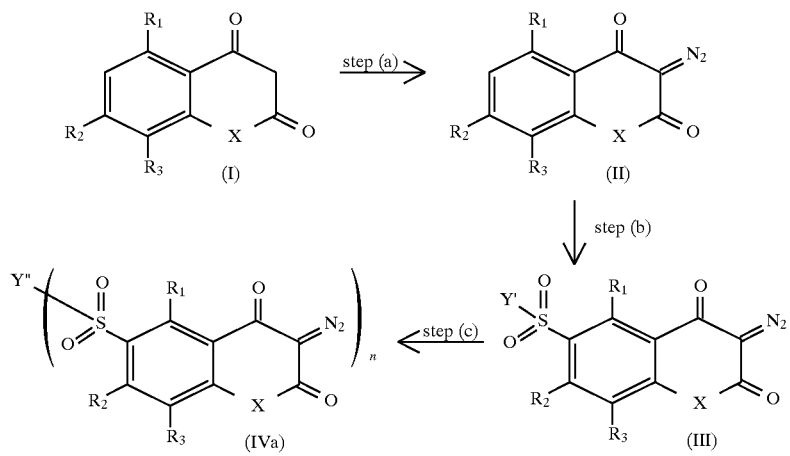

In Scheme I, steps (a) through (c) correspond to those steps (a) through (c) mentioned herein. The substituent Y' in Formula III is selected from the group consisting of bromine, chlorine, and fluorine; and the substituent Y" in Formula IVa is selected from the group consisting of a phenolic resin, and a ballast group having the formula: $R_4$—(O)$_m$—, or $R_5$—($R_6$N)$_m$—, where $R_4$, $R_5$, $R_6$, and m are as defined above. The substituents $R_1$, $R_2$, $R_3$, X, and n in Formulae I through IV are as defined above.

In step (a), the diazo transfer reaction can be carried out using any of the well-known methods in the art. For instance, a description of a diazo transfer reaction may be found in U.S. Pat. No. 4,942,225 and in Org. Syn. Collective Vol. 5, pp. 179–183; both of which are incorporated herein by reference in their entirety. It has now been found that p-toluenesulfonyl (tosyl) azide works as an effective diazo transfer agent to form the diazo compound II as shown in Scheme I.

The amount of tosyl azide used in step (a) is generally stoichiometric amount, i.e., one mole of azide per mole of the starting material I. It is preferable that slight excess of tosyl azide is employed in order to achieve complete conversion of starting material to the diazo compound II. It is also preferable that the reaction is carried out in the presence of a suitable base. Examples of such base include triethylamine, pyridine, imidazole, and the like.

The temperature at which step (a) is conducted ranges from about 10° C. to about 50° C., preferably from about 20° C. to about 40° C. The pressure in this step (a) is not critical and can be subatmospheric, atmospheric, or super atmospheric. The reaction times in step (a) will generally range from about ¼ hour to about 4 hours or longer and sometimes under an inert atmosphere such as nitrogen or argon. Using the procedure of step (a) outlined herein, the substituted benzo-heterocyclic β-keto-enol compound (Formula I, Scheme I) undergoes suitable diazo transfer reaction to form the corresponding diazo diketo compound, Formula II, Scheme I.

In step (b), the diazo compound is halosulfonated to form the corresponding halosulfonyl diazo compound, Formula III, Scheme I. A wide variety of known methods can be used to halosulfonate the diazo compound, II. For example, diazo compound, II may first be sulfonated using any of the sulfonating agents such as sulfuric acid, fuming sulfuric acid, or sulfur trioxide. In a subsequent step, the sulfonic acid formed is halogenated using phosphorus pentahalides such as phosphoruspentachloride to form the halosulfonated compound, III. A description of the sulfonation reactions may be found in Gilbert "Sulfonation and Related Reactions," pp. 62–83, 87–124, Interscience, New York, 1965; incorporated herein by reference in its entirety.

Advantageously, it has now been found that diazo compound, II can be halosulfonated directly and selectively at 6- position in a single step (i.e., step (b)) using a halosulfonic acid such as chlorosulfonic acid, bromosulfonic acid, or fluorosulfonic acid. The reaction proceeds smoothly and results in halosulfonyl diazo compound, III in quantitative yields. The amount of halosulfonic acid employed in this step is generally stoichiometric, however, slight excess of the halosulfonic acid results in high yields of the product, III. A particularly preferred halosulfonic acid is chlorosulfonic acid.

The temperature at which step (b) is conducted ranges from about 30° C. to about 80° C., preferably from about 40° C. to about 60° C. The pressure in this step (b) is not critical and can be subatmospheric, atmospheric, or super atmospheric. The reaction times in step (b) will generally range from about 40 hours to about 60 hours or longer and sometimes under an inert atmosphere such as nitrogen or argon. Using the procedure of step (b) outlined herein, the substituted diazo diketo compound (Formula II, Scheme I) undergoes suitable halosulfonation reaction to form the corresponding halosulfonyl diazo diketo compound, Formula III, Scheme I.

In step (c), the halosulfonyl diazo compound, III is subjected to suitable substitution reaction in the presence of an alcohol or an amine to form the corresponding sulfonic acid ester or amide of fused benzo-heterocyclic diazo diketo compound, Formula IVa, Scheme I. A wide variety of known methods in the art can be used to form the sulfonic acid ester or amide, Formula IVa. For example, halosulfonyl diazo compound, III may be reacted with a variety of alcohols or amines to form the corresponding sulfonic acid ester or amide, Formula IVa in the presence of a suitable base as an acid scavenger.

Any base which will function as an acid scavenger may be used in step (c). A suitable base includes an inorganic base such as a metal hydroxide, preferably an alkali metal hydroxide, an alkali metal carbonate, e.g., $K_2CO_3$; an alkali metal alkoxide (an ionic organic base), such as $NaOCH_3$, $KOC(CH_3)_3$, etc.; an alkali metal organic salt (an ionic organic base) such as potassium acetate, etc.; and an amine (a non-ionic organic base) such as pyridine, or a tri-lower-alkylamine, e.g., tripropylamine, trimethylamine, triethylamine, a hindered base such as 1,4-diazabicyclo [2.2.2]octane, and 4-dimethylaminopyridine, etc. Ammonia can also be used as a base in step (c) of the process of the present invention.

Advantageously, it has now been found that organic bases described herein are particularly suitable bases in step (c) of the process of the present invention. More particularly, the hindered bases such as 1,4-diazabicyclo[2.2.2]octane and 4-dimethylaminopyridine are preferred bases in step (c) of the process of the present invention.

A variety of alcohols and amines, i.e., aromatic or aliphatic mono- or polyalcohols and amines mentioned herein may be used as suitable alcohols or amines in step (c) of the process of the present invention. Particularly, preferred compounds are the alcohols mentioned herein to form the corresponding sulfonic acid esters, Formula IVa. Appropriate amounts of the desired alcohol are used in step (c) to form the fully substituted or partially substituted sulfonic acid esters, IVa as described herein. In general, a stoichiometric amount or slight excess of the alcohol is employed in order to obtain high yields of the sulfonic acid ester, IVa.

The temperature at which step (c) is conducted ranges from about 10° C. to about 50° C., preferably from about 20° C. to about 40° C. The pressure in this step (c) is not critical and can be subatmospheric, atmospheric, or super atmospheric. The reaction times in step (c) will generally range from about 2 hours to about 8 hours or longer and sometimes under an inert atmosphere such as nitrogen or argon. Using the procedure of step (c) outlined herein, the substituted halosulfonyl diazo diketo compound (Formula III, Scheme I) undergoes suitable substitution reaction to form the corresponding sulfonic acid ester or amide diazo diketo compound, Formula IVa, Scheme I. Particularly, preferred sulfonic acid esters or amides, IVa that can be formed by the process of this invention are the 3-diazo-4-oxo-3,4-dihydrocoumarin-6-sulfonic acid esters as described herein.

This invention is further illustrated by the following examples which are provided for illustration purposes and in no way limit the scope of the present invention.

EXAMPLES (General)

In the Examples that follow, the following abbreviations are used:

THPE - 1',1',1'-Tris(4-hydroxyphenyl)ethane
THF - Tetrahydrofuran
PHS - Poly(4-hydroxystyrene)
HPLC - High performance liquid chromatography
IR - Infrared spectroscopy
NMR - Nuclear magnetic resonance spectroscopy, usually of either proton, $^1$H; and/or carbon 13, $^{13}$C nuclei.
DSC - Differential scanning calorimetry
MS-APCI - Mass spectroscopy-Atmospheric pressure chemical ionization
MS-DIP - Mass spectrometer-Direct insertion probe
UV-Vis - Ultraviolet-Visible Spectroscopy General Analytical Techniques Used for the Characterization: A variety of analytical techniques were used to characterize the 3,4-dihydrocoumarin compounds of the present invention which included the following:

IR: IR spectra of samples were taken using a Nicolet 205SXB FT-IR spectrometer.

NMR: $^1$H and $^{13}$C NMR spectra were recorded on a Bruker 400 MHz spectrometer with 5 mm probes at 400 and 100 MHz, respectively.

HPLC: HPLC was performed on a Hewlett Packard 1090 Liquid Chromatograph as follows: Mobile phase - methanol/0.1% acetic acid in water (gradient method); UV detector @254 nm; column - Alltech Allsphere ODS-2,5 micron, 150 mm×4.6 mm.

DSC: A Perkin Elmer 7700 DSC was used to determine the $T_m$ (melting point, peak value) of the photoactive compounds of this invention. The heating rate was maintained at 10° C./minute, generally, over a temperature range of 50° C. to 400° C. The flow rate of nitrogen or air is maintained at 20 mL/min.

MS-APCI of samples were taken using a Finnigan SSQ7000 Mass spectrometer.

MS-DIP of samples were taken using a Finnigan 4500 Mass spectrometer.

UV-Vis of samples were taken using a Hewlett Packard Vectra 486/33VL UV-Vis spectrophotometer

Example 1

Preparation of 3-Diazo-4-oxo-3,4-dihydrocoumarin

To a 100 mL round-bottom flask fitted with a mechanical stirrer, nitrogen inlet and bubbler was charged 4-hydroxycoumarin (3.1 g, 18.8 mmol) dissolved in dry THF (21.6 g) and triethylamine (1.8 g). A solution of p-toluenesulfonyl azide (5.3 g, 28.3 mmol) in dry THF (14.4 g) was then added to this solution dropwise over a period of 15 minutes. The reaction was continued until all of 4-hydroxycoumarin had reacted as monitored by HPLC (ca. 2.0 hours). The precipitated reaction product was filtered on a small Buchner funnel and the filtrate was packed in powdered dry ice to produce a second crop of crystals which were also isolated by filtration. The combined filtercakes were dried overnight under vacuum at 60° C. to obtain orange colored crystals of 3-diazo-4-oxo-3,4-dihydrocoumarin; yield 2.5 g (70.6% yield). The crude product was further purified by dissolving it in 75.0 g of acetone and precipitating by pouring into 150.0 g ice-water yielding pale yellow crystals. The product was characterized by $^{13}$C NMR, and DSC. A sample recrystallized from acetone-water melted at 159.5° C.; $^{13}$C-NMR in DMSO-d$_6$ solvent showed 9 singlet lines at the following chemical shifts, in ppm: 173.748, 157.754, 153.316, 136.239, 125.231, 125.063, 118.696, 117.741, 77.022.

Example 2

Preparation of 6-Chlorosulfonyl-3-diazo-4-oxo-3,4-dihydrocoumarin

A 250 mL three-necked round-bottom flask equipped with a magnetic stirrer, water bath, nitrogen inlet and bubbler, thermometer and temperature controller was charged with 3-diazo-4-oxo-3,4-dihydrocoumarin (10.1 g, 53.7 mmol) prepared in accordance with Example 1 and chlorosulfonic acid (75.1 g). The reaction mixture was then heated to 50° C. and maintained at 50° C. for 42 hours, during which time HPLC analysis showed 99% conversion. The reaction was allowed to cool and was poured slowly, in portions, with stirring, into 420 g ice cold ethanol (the temperature of the ethanol slurry was kept below 10° C. throughout the addition). The ethanolic slurry was filtered, and dried in an oven overnight under vacuum at 58° C. to yield 12.5 g of pure 6-chlorosulfonyl-3-diazo-4-oxo-3,4-dihydrocoumarin (81% yield). The product was characterized by $^{13}$C NMR, DSC and UV-Vis. The results are as follows: the vacuum dried sample melted at 184.7° C. $^{13}$C-NMR in THF-d$_8$ solvent, showed 9 singlet lines at the following chemical shifts, in ppm: 172.693, 1158.932, 157.050, 141.502, 134.467, 126.202, 121.104, 121.091, 77.983. The UV absorption spectrum of the product in THF solvent was determined at a dilution factor, DF=109,182.05 yielding, λ1 max=232 nm, ε1 max=29,532.1 liters/mole cm; and λ2max= 288 nm, ε2 max=9,472.8 liters/mole cm.

Example 3

Preparation of Bis(6-sulfonyl-3-diazo-4-oxo-3,4-dihydrocoumarin)bisphenol A

This Example illustrates the method of attaching ballast groups to the photoactive compounds of the present invention. A 500 mL three-necked, round-bottom flask equipped with a magnetic stirrer, water bath, thermocouple, nitrogen inlet and bubbler was charged with a solution of bisphenol A (3.9 g, 16.9 mmol) in THF (50.0 g). Triethylamine (8.3 g) was then added to this solution dropwise and the reaction mixture was allowed to stir for five minutes. A solution of 6-chlorosulfonyl-3-diazo-4-oxo-3,4-dihydrocoumarin (10.078 g, 35.2 mmol; from Example 2) in THF (196 g) was added dropwise and the reaction was allowed to stir at room temperature for about four hours, the reaction mixture was then filtered to remove any insoluble impurities. The filtrate was precipitated in nine times its weight of petroleum ether. The resulting slurry was filtered and the filtercake was dried overnight at 60° C. under vacuum, providing 12.5 g pink solids. The crude product was dissolved in 554 g chloroform. The solution was washed with 378 g water and dried over anhydrous magnesium sulfate. The solution was filtered and the filtrate was stirred with 1.8 g of decolorizing charcoal and was filtered. The product was precipitated by pouring over 2122 g of petroleum ether, filtered, and dried in a vacuum oven, overnight at 60° C.; yield 8.9 g (72%). The product was characterized by $^{13}$C NMR, DSC and UV-Vis. The product melted with decomposition at 200° C. $^{13}$C-NMR in CDCl$_3$ solvent showed 15 singlet lines at the following chemical shifts, in ppm: 171.999, 156.833, 156.475, 149.533, 147.198, 135.124, 132.912, 128.263, 127.444, 121.742, 119.466, 119.291, 77.206, 42.700, 30.692. The UV absorption spectrum of the product in THF solvent was determined at a dilution factor, DF=116,494.72 yielding, λ1 max=228 nm, ε1 max=84,528.6 liters/mole cm; and λ2 max=288 nm, ε2 max=20,956.83 liters/mole cm.

Example 4

Preparation of 1',1',1',-Tris-4-(3-diazo-4-oxo-3,4-dihydrocoumarin-6-sulfonyloxyphenyl)ethane Example 3 was substantially repeated in Example 4 with the exception that the type of ballast group and amounts of materials used were as set forth below:

| Materials | Amount |
| --- | --- |
| THPE | 0.7 g (2.3 mmol) |
| 6-Chlorosulfonyl-3-diazo-4-oxo-3,4-dihydro-coumarin (from Example 2) | 2 g (7 mmol) |
| Triethylamine | 1.7 g (16.4 mmol) |
| THF | 45 g |

The product was isolated as 2.4 g (97% yield) of pink solids. Recrystallization from chloroform-petroleum ether, then toluene-petroleum ether yielded white crystals. The product was characterized by $^{13}$C NMR, DSC, and UV-Vis. The results are as follows: the product melted at 218.7° C. $^{13}$C-NMR in DMSO-d$_6$ solvent showed 15 singlet lines at the following chemical shifts, in ppm: 172.374, 156.888, 156.763, 142.277, 147.048, 134.875, 130.639, 129.829, 125.594, 121.766, 120.148, 119.383, 77.998, 51.330, 29.799. The UV-V is absorption spectrum of the product in THF solvent was determined at a dilution factor, DF=121, 993.22 yielding, λ1 max=228 nm, ε1 max=115,055.73 liters/ mole cm; and λ2 max=288 nm, ε2 max=28,927.91 liters/ mole cm.

Example 5

Preparation of 4,4'-Bis (3-diazo-4-oxo-3,4-dihydrocoumarin-6-sulfonyloxy)benzophenone Example 3 was substantially repeated in Example 5 with the exception that the type of ballast group and amounts of materials used were as set forth below:

| Materials | Amount |
| --- | --- |
| 4,4'-dihydroxy-benzophenone | 0.7 g (3.4 mmol) |
| 6-Chlorosulfonyl-3-diazo-4-oxo-3,4-dihydro-coumarin (from Example 2) | 2 g (7 mmol) |
| Triethylamine | 1.7 g (16.5 mmol) |
| THF | 50 g |

The product was isolated as 1.9 g (78% yield) of pink solids. The product was characterized by $^{13}$C NMR, and DSC. The results are as follows: the product melted with decomposition above 175° C. $^{13}$C-NMR in DMSO-d$_6$ solvent showed 14 singlet lines at the following chemical shifts, in ppm: 193.183, 172.343, 157.034, 156.783, 151.555, 135.702, 134.965, 131.779, 130.502, 125.714, 122.339, 120.297, 119.585, 78.069.

Example 6

Preparation of 2,3,4,-Tris (3-diazo-4-oxo-3,4-dihydrocoumarin-6-sulfonyloxy)benzophenone Example 3 was substantially repeated in Example 6 with the exception that the type of ballast group and amounts of materials used were as set forth below:

| Materials | Amount |
| --- | --- |
| 2,3,4,-Trihydroxy-benzophenone | 2.1 g (9.2 mmol) |
| 6-Chlorosulfonyl-3-diao-4-oxo-3,4-dihydro-coumarin (from Example 2) | 10.2 g (35.5 mmol) |
| Triethylamine | 8.3 g (82 mmol) |
| THF | 230 g |

The product was isolated as 8.3 g (78% yield) of crystalline product. The product was characterized by $^{13}$C NMR, and DSC. The results are as follows: the product melted at 221° C. $^{13}$C-NMR in DMSO-d$_6$ solvent showed 30 singlet lines at the following chemical shifts, in ppm: 189.986 172.104, 172.015, 171.804, 157.390, 157.126, 156.995, 156.642 156.572, 143.508, 135.054, 134.865, 134.762, 133.699, 131.071, 129.803, 129.780, 129.580, 128.633, 126.050, 125.745, 120.240, 120.199, 120.077, 119.586, 119.495, 119.181, 117.422, 78.212, 78.120.

Example 7

Mixtures of 1'-Mono, 1',1'-Bis-, and 1',1',1'-Tris Sulfonate Esters of 4-(3-diazo-4-oxo-6-(3,4-dihydrocoumarin)sulfonyloxyphenyl)ethane.

Example 7 illustrates the preparation of a mixture of fully and partially substituted ballast molecule with a photoactive compound. Example 3 was substantially repeated in Example 7 with the exception of modifications in procedure as set forth below. A 1 liter three-necked round-bottom flask equipped with a mechanical stirrer, water bath, thermometer, nitrogen inlet and bubbler was charged with a solution of THPE (8.7 g, 28.4 mmol) in THF (130 g). Triethylamine (20.7 g) was added dropwise and the reaction mixture was allowed to stir for an additional 3–5 minutes. A solution of 6-chlorosulfonyl-3-diazo-4-oxo-3,4-dihydrocoumarin (16.3 g, 57 mmol: prepared in accordance with Example 2) in THF (270 g) was added dropwise, and the reaction was allowed to stir at room temperature. After one hour, the reaction mixture was cooled in an ice bath and neutralized by dropwise addition of conc. HCl (16.36 g) while maintaining the temperature of the reaction mixture at about 12° C. The reaction solution was filtered to remove any insoluble impurities. The filtrate was precipitated, with stirring, into five times its weight of hexane (1930 g), filtered and dried in a vacuum oven overnight at 58° C; yield 21.56 g of yellow solids (97%). The product was taken up in chloroform, washed with water, dried over sodium sulfate, and treated with decolorizing charcoal. Precipitation into petroleum ether provided off-white crystals. The product was a mixture of mono-, bis-, and tris-sulfonate esters of THPE and the diazo-dihydrocoumarin. The composition of the mixture was determined to be mono- 8 %, bis- 42%, and tris- 50% by HPLC. The product was further characterized by $^{13}$C NMR, DSC, and UV-Vis and the results are as follows: the product melted at 219.1° C. $^{13}$C-NMR in DMSO-$d_6$ solvent showed 32 singlet lines at the following chemical shifts, in ppm: 172.357, 156.884, 156.858, 156.780, 156.753, 155.578, 155.277, 148.389, 147.270, 147.054, 146.833, 134.874, 130.743, 130.656, 129.828, 129.027, 125.596, 121.759, 121.463, 121.161, 120.139, 120.100, 119.384, 114.792, 114.542, 77.978, 51.337, 50.864, 50.363, 30.190, 29.994, 29.806. The UV-Vis absorption spectrum of the product in THF solvent was determined at a dilution factor, DF=158,000 yielding, $\lambda 1$ max=230 nm, $\epsilon 1$ max=91,500 liters/mole cm; and $\lambda 2$ max=288 nm, $\epsilon 2$ max=23,000 liters/mole cm.

Example 8

Preparation of Poly(4-hydroxystyrene)-3-diazo-4-oxo-3,4-dihydrocoumarin-6-sulfonate Example 8 illustrates the preparation of a partially substituted polymeric product with a photoactive compound. Example 3 was substantially repeated in Example 8 with the exception of modifications in procedure as set forth below. A 500 mL three-necked round-bottom flask equipped with a magnetic stirrer, water bath, thermometer, nitrogen inlet and bubbler was charged with a solution of PHS (13.3 g, 110 mmol based on monomer repeat units) in THF (170 g). Triethylamine (6.8 g) was added dropwise and the reaction mixture was allowed to stir for an additional 3–5 minutes. A solution of 6-chlorosulfonyl-3-diazo-4-oxo-3,4-dihydrocoumarin (1.6 g, 5.6 mmol) in THF (124 g) was added dropwise and the reaction was allowed to stir at room temperature. After one hour, HPLC analysis showed no residual starting material. The reaction mixture was cooled in an ice bath and neutralized by dropwise addition of conc. HCl (8 g) while maintaining the reaction temperature around 12° C. The reaction mixture was filtered to remove any insoluble impurities. The filtrate was precipitated, with stirring, into ten times its weight of hexane. The resulting slurry was filtered, dried in a vacuum oven overnight at 60° C.; yield 11.2 g of white solids (77% yield). The product was characterized by UV-Vis as follows: the UV-Vis absorption spectrum of the product in THF solvent was determined at a dilution factor, DF=46,948.36 yielding, $\lambda 1$ max=230 mn, $\epsilon 1$ max=91,245.78 liters/mole cm; and $\lambda 2$ max=282 nm, $\epsilon 2$ max=29,969.20 liters/mole cm (based on a repeat unit MW=2633.2).

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A process for preparing sulfonic acid ester or amide of fused benzo-heterocyclic diazo diketo compounds comprising the steps of:

(a) subjecting a substituted benzo-heterocyclic β-keto-enol compound to suitable diazo transfer conditions in the presence of a diazo transfer agent for a sufficient period of time and under suitable conditions of temperature and pressure to form the corresponding diazo diketo compound;

(b) subjecting said diazo diketo compound to suitable halosulfonation conditions in the presence of a halosulfonation agent for a sufficient period of time and under suitable conditions of temperature and pressure to form the corresponding halosulfonyl diazo diketo compound; and (c) subjecting said halosulfonyl diazo diketo compound to suitable substitution reaction in the presence of an alcohol or an amine and a suitable base for a sufficient period of time and under suitable conditions of temperature and pressure to form the corresponding sulfonic acid ester or amide of the fused benzo-heterocyclic diazo diketo compound.

2. The process as set forth in claim 1 wherein said substituted benzo-heterocyclic β-keto-enol compound has the formula:

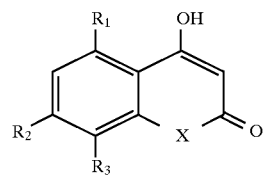

wherein:

(a) X is either oxygen or sulfur;

(b) $R_1$, $R_2$, and $R_3$ are the same or different and are independently selected from the group consisting of:
   hydrogen,
   fluorine, chlorine, bromine, or iodine,
   linear or branched alkyl and fluoroalkyl groups having the formula
   $C_qH_xF_y$, where q is an integer from 1 to 8, x and y are integers from 0 to 2q+1, and the sum of x and y is 2q+1,
   aryl having 6 to 10 carbon atoms,
   aralkyl having 7 to 10 carbon atoms,
   alkoxy having 1 to 8 carbon atoms,
   aryloxy having 6 to 10 carbon atoms, and
   aralkyloxy having 7 to 10 carbon atoms.

3. The process as set forth in claim 1 wherein said halosulfonyl diazo diketo compound has the formula:

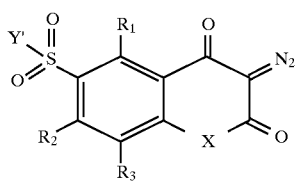

wherein:
(a) X is either oxygen or sulfur;
(b) Y' is bromine, chlorine, or fluorine; and
(c) $R_1$, $R_2$, and $R_3$ are the same or different and are independently selected from the group consisting of:
hydrogen,
fluorine, chlorine, bromine, or iodine,
linear or branched alkyl and fluoroalkyl groups having the formula
$C_qH_xF_y$, where q is an integer from 1 to 8, x and y are integers from 0 to 2q+1, and the sum of x and y is 2q+1,
aryl having 6 to 10 carbon atoms,
aralkyl having 7 to 10 carbon atoms,
alkoxy having 1 to 8 carbon atoms,
aryloxy having 6 to 10 carbon atoms, and
aralkyloxy having 7 to 10 carbon atoms.

4. The process as set forth in claim 1 wherein said sulfonic acid ester or amide of fused benzo-heterocyclic diazo diketo compound has the formula:

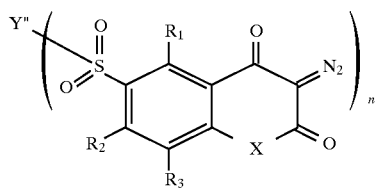

wherein:
(a) X is either oxygen or sulfur;
(b) Y" is selected from the group consisting of a phenolic resin, and a ballast group having the formula:
$R_4$—(O)$_m$—, or $R_5$—($R_6$N)$_m$—, where
(i) $R_4$, and $R_5$ are the same or different and are independently selected from the group consisting of:
alkyl having 1 to 16 carbon atoms and valence of m,
aryl having 6 to 24 carbon atoms and valence of m, and
aralkyl having 7 to 24 carbon atoms and valence of m;
(ii) $R_6$ is selected from the group consisting of:
hydrogen,
alkyl having 1 to 16 carbon atoms,
aryl having 6 to 24 carbon atoms, and
aralkyl having 7 to 24 carbon atoms; and
(iii) m is an integer having a value of 1 to 10;; and
(c) $R_1$, $R_2$, and $R_3$ are the same or different and are independently selected from the group consisting of:
hydrogen,
fluorine, chlorine, bromine, or iodine,
linear or branched alkyl and fluoroalkyl groups having the formula
$C_qH_xF_y$, where q is an integer from 1 to 8, x and y are integers from 0 to 2q+1, and the sum of x and y is 2q+1,
aryl having 6 to 10 carbon atoms,
aralkyl having 7 to 10 carbon atoms,
alkoxy having 1 to 8 carbon atoms,
aryloxy having 6 to 10 carbon atoms, and
aralkyloxy having 7 to 10 carbon atoms; and
(d) n is an integer having a value of 1 to 10.

5. The process as set forth in claim 4 wherein X is oxygen.
6. The process as set forth in claim 4 wherein X is sulfur.
7. The process as set forth in claim 1 wherein in step (a) the temperature is from about 10° C. to about 50° C. and the pressure is atmospheric; in step (b) the temperature is from about 30° C. to about 80° C. and the pressure is atmospheric; and in step (c) the temperature is from about 10° C. to about 50° C. and the pressure is atmospheric.
8. A process for preparing sulfonic acid esters of 3-diazo-4-oxo-3,4-dihydrocoumarins comprising the steps of:
(a) subjecting a substituted 4-hydroxycoumarin to suitable diazo transfer conditions in the presence of a diazo transfer agent for a sufficient period of time and under suitable conditions of temperature and pressure to form the corresponding 3-diazo-4-oxo-3,4-dihydrocoumarin;
(b) subjecting said diazo coumarin to suitable chlorosulfonation conditions in the presence of a chlorosulfonation agent for a sufficient period of time and under suitable conditions of temperature and pressure to form the corresponding chlorosulfonyl-3-diazo-4-oxo-3,4-dihydrocoumarin; and
(c) subjecting said chlorosulfonyl diazo dihydrocoumarin to suitable substitution reaction in the presence of an alcohol and a suitable acid scavenger for a sufficient period of time and under suitable conditions of temperature and pressure to form the corresponding sulfonic acid ester of 3-diazo-4-oxo-3,4-dihydrocoumarin.

9. The process as set forth in claim 8 wherein said chlorosulfonyl-3-diazo-4-oxo-3,4-dihydrocoumarin has the formula:

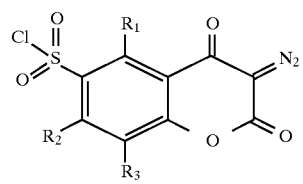

wherein:
(a) $R_1$, $R_2$, and $R_3$ are the same or different and are independently selected from the group consisting of:
hydrogen,
fluorine, chlorine, bromine, or iodine,
linear or branched alkyl and fluoroalkyl groups having the formula
$C_qH_xF_y$, where q is an integer from 1 to 8, x and y are integers from 0 to 2q+1, and the sum of x and y is 2q+1,
aryl having 6 to 10 carbon atoms,
aralkyl having 7 to 10 carbon atoms,
alkoxy having 1 to 8 carbon atoms,
aryloxy having 6 to 10 carbon atoms, and
aralkyloxy having 7 to 10 carbon atoms.

10. The process as set forth in claim 8 wherein said sulfonic acid ester of 3-diazo-4-oxo-3,4-dihydrocoumarin has the formula:

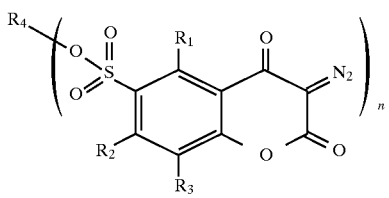

wherein:
(a) $R_1$, $R_2$, and $R_3$ are the same or different and are independently selected from the group consisting of:
hydrogen,
fluorine, chlorine, bromine, or iodine,
linear or branched alkyl and fluoroalkyl groups having the formula
$C_qH_xF_y$, where q is an integer from 1 to 8, x and y are integers from 0 to 2q+1, and the sum of x and y is 2q+1;,
aryl having 6 to 10 carbon atoms,
aralkyl having 7 to 10 carbon atoms,
alkoxy having 1 to 8 carbon atoms,
aryloxy having 6 to 10 carbon atoms, and
aralkyloxy having 7 to 10 carbon atoms;
(b) $R_4$ is selected from the group consisting of:
monovalent or polyvalent alkyl having 1 to 16 carbon atoms,
monovalent or polyvalent aryl having 6 to 24 carbon atoms,
monovalent or polyvalent aralkyl having 7 to 24 carbon atoms, and
a phenolic resin; and
(c) n is an integer having a value of 1 to 8.

11. The process as set forth in claim 8 wherein in step (a) the temperature is from about 10° C. to about 50° C. and the pressure is atmospheric; in step (b) the temperature is from about 30° C. to about 80° C. and the pressure is atmospheric; and in step (c) the temperature is from about 10° C. to about 50° C. and the pressure is atmospheric.

12. The process as set forth in claim 8 wherein in step (a) the temperature is from about 20° C. to about 40° C. and the pressure is atmospheric; in step (b) the temperature is from about 40° C. to about 60° C. and the pressure is atmospheric; and in step (c) the temperature is from about 20° C. to about 40° C. and the pressure is atmospheric.

13. The process as set forth in claim 8 wherein said diazo transfer agent is p-toluenesulfonyl azide.

14. The process as set forth in claim 8 wherein said chlorosulfonating agent is chlorosulfonic acid.

15. The process as set forth in claim 8 wherein in step (c) said acid scavenger is a hindered amine.

16. The process as set forth in claim 15 wherein said hindered amine is selected from the group consisting of 1,4-diazabicyclo[2.2.2]octane and 4-dimethylaminopyridine.

17. The process as set forth in claim 8 wherein said alcohol is a phenolic resin selected from the group consisting of novolak resins; poly(4-hydroxystyrene); copolymers of hydroxystyrene and a member selected from the group consisting of acrylate, methacrylate and mixtures thereof; poly(hydroxystyrene-co-t-butyloxycarbonyloxystyrene); poly(hydroxystyrene-co-hydroxymethylstyrene); poly(hydroxystyrene-co-acetoxymethylstyrene); and alkyl substituted polyvinyl phenols.

18. The process as set forth in claim 17 wherein said phenolic resin is poly(4-hydroxystyrene).

19. The process as set forth in claim 10 wherein $R_1$ to $R_3$ are hydrogen, and $R_4$ is selected from the group consisting of:

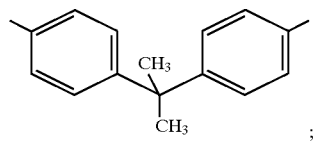
;

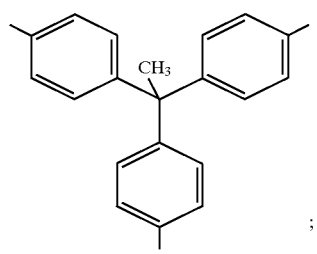
;

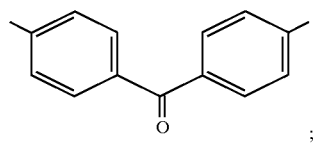
;

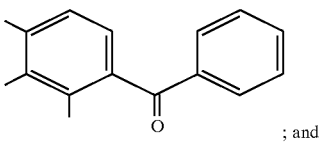
; and

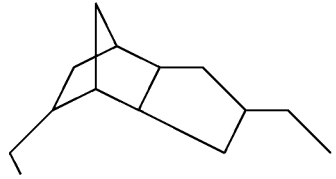

* * * * *